United States Patent [19]
Williamitis et al.

[11] Patent Number: 5,185,006
[45] Date of Patent: * Feb. 9, 1993

[54] LUBRICATED METAL ARTICLES AND ASSEMBLY CONTAINING SAME

[75] Inventors: Victor A. Williamitis, Dayton; David E. Spielvogel, Springboro, both of Ohio

[73] Assignee: Becton, Dickinson and Company, Franklin Lakes, N.J.

[*] Notice: The portion of the term of this patent subsequent to Feb. 27, 2007 has been disclaimed.

[21] Appl. No.: 628,139

[22] Filed: Dec. 17, 1990

[51] Int. Cl.$^5$ .................... A61M 5/32; A61M 25/00
[52] U.S. Cl. .................... 604/265; 428/450; 528/30; 528/33; 264/130; 264/131
[58] Field of Search .......... 252/9; 528/20–22, 528/31, 33, 38; 106/287.11, 287.14, 287.16, 36; 604/264–266; 428/450, 447; 264/130, 131

[56] References Cited

U.S. PATENT DOCUMENTS

| | | | |
|---|---|---|---|
| 3,574,673 | 4/1971 | Schweiger . | |
| 4,455,415 | 6/1984 | Panster et al. | 528/39 |
| 4,588,398 | 5/1986 | Daugherty et al. | 604/265 |
| 4,664,657 | 5/1987 | Williamitis et al. | 604/265 |
| 4,664,657 | 5/1987 | Williamitis . | |
| 4,720,521 | 1/1988 | Spielvogel et al. . | |
| 4,767,414 | 8/1988 | Williams et al. . | |
| 4,904,433 | 2/1990 | Williamitis | 604/265 |
| 4,904,433 | 2/1990 | Williamitis . | |
| 4,954,599 | 9/1990 | Panster et al. | 528/38 |
| 5,003,024 | 3/1991 | Panster et al. | 528/30 |

FOREIGN PATENT DOCUMENTS

| | | |
|---|---|---|
| 1377776 | 6/1972 | United Kingdom . |
| 1506226 | 4/1978 | United Kingdom . |

OTHER PUBLICATIONS

*Organic Chemistry*, Chapter Nine "Alkers and Alkgnes", Willard Grant Press, 1979, pp. 418–419.
Bailar et al., editors, *Comprehensive Inorganic Chemistry: volume 1;* "Silicon" (Rochan, author), pp. 1458–1460, 1973.
"Lubrication: A Technical Publication Devoted to the Selection and us of Lubricants"; Jun. 1957, vol. 43, No. 6, The Texaco Company.

*Primary Examiner*—C. Fred Rosenbaum
*Assistant Examiner*—Chalin Smith
*Attorney, Agent, or Firm*—Richard E. Brown

[57] ABSTRACT

A metal article has a coating of a noncuring polar lubricant. Preferred articles are of stainless steel and may be cutting devices such as needles, lancets and cannulas or sliding devices such as stylets and guidewires. Preferred noncuring polar lubricants are polysiloxanes terminated with a polar group. Particularly preferred lubricants are aminoalkyl or carboxyalkyl polysiloxanes. The lubricated metal article may be in a sliding relationship with a plastic article such as a catheter-guidewire or a catheter-cannula assembly. The plastic portion of the assembly may also include a lubricant.

15 Claims, 1 Drawing Sheet

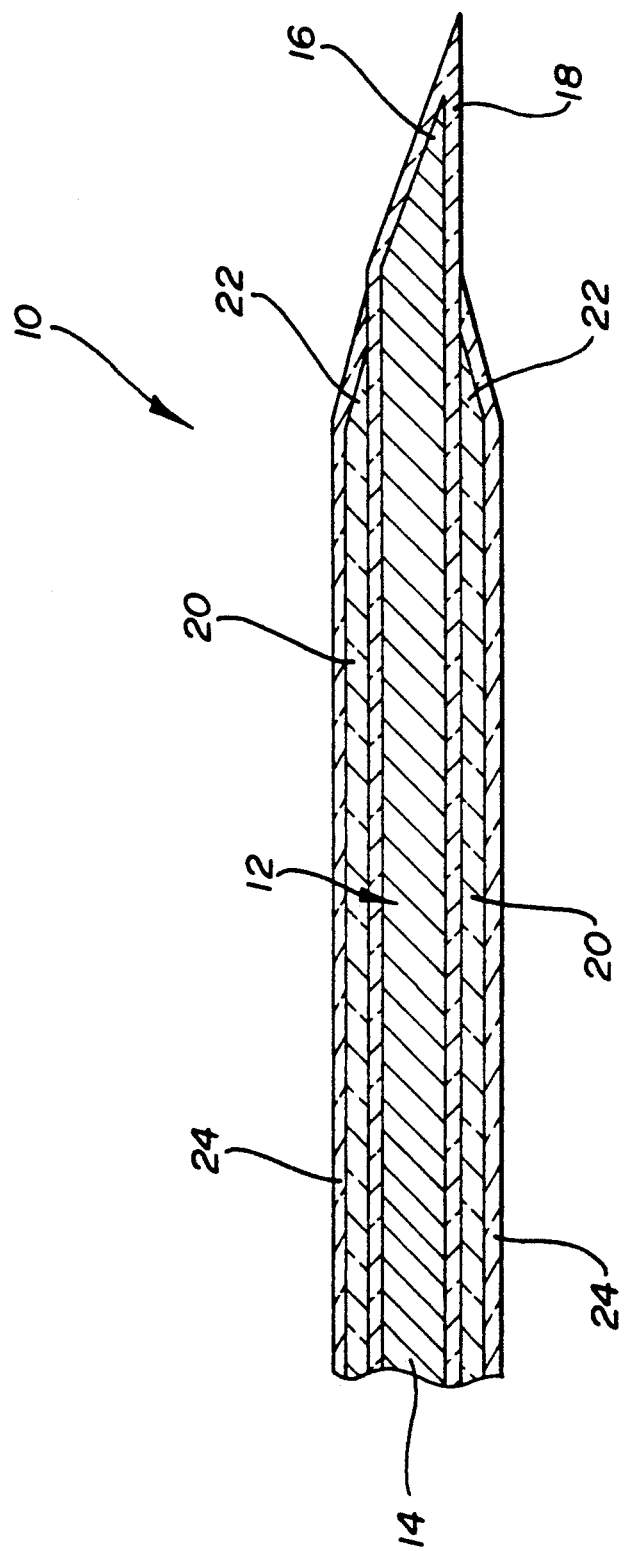

LUBRICATED METAL ARTICLES AND ASSEMBLY CONTAINING SAME

BACKGROUND OF THE INVENTION

1. Field of the Invention

This invention relates to medical articles, and more particularly, relates to lubricated metal articles contemplated for penetration or cutting of the skin or use with a plastic article in an assembly.

2. Background of the Invention

Many occasions arise when it is necessary to puncture the skin with a metal device, generally of stainless steel, having a sharp point or edge. Representative of such devices are surgical blades, lancets, cannulas, catheter insertion devices, guidewires and the like. In other cases, a cutting edge, such as a razor blade, is advanced across a skin surface.

When such a device is advanced across the skin or inserted through the skin, the skin is stretched and a certain amount of pain is experienced. It has been common practice for many years to lubricate the device to minimize pain.

Noncuring, nonpolar silicones, such as the DC ®360 series of medical grade polydimethylsiloxanes (PDMS) available from Dow Corning Co. have been used. These products, while widely used, have the disadvantage of ease of wipe away or migration from the surface to which they have been applied. Another problem with these lubricants is adhesion which develops over time when metal to plastic or two plastic surfaces are engaged by an interference fit. For plastic syringes and associated plunger, Williams et al., in U.S. Pat. No. 4,767,414, discloses that plasma treatment of one of the surfaces and the oil overcomes adhesion. For a catheter cannula assembly, Williamitis et al. discloses in U.S. Pat. No. 4,664,657 that adhesion can be mitigated if the PDMS is of high viscosity.

The problem of wipe-away is particularly severe when metal surfaces are lubricated with noncuring PDMS. For example, in the case of a hypodermic needle coated with PDMS, the coating may be substantially removed due to frictional wiping forces during penetration of the skin and vein, making subsequent removal of the needle difficult and painful to the patient. Migration during storage and inadvertent removal during processing is also a concern.

Spielvogel, in U.S. Pat. No. 4,720,521, discloses overcoming the migration problem by including a noncuring PDMS in a curing composition. The noncuring lubricating PDMS is occluded in a mixture of at least three curing silicones which adhere to a metal surface.

U.S. Pat. No. 3,574,673 to Schweiger discloses curing organopolysiloxanes used as friction reducing coatings on blades. These products are copolymers of alkylamine modified methoxysiloxanes which undergo , moisture curing at ambient temperature to a gelatinous film. Representative of this class of materials is the commercially available product MDX-4-4159. Depending on ambient humidity, MDX-4-4159 requires at least a four hour precure before assembly and from two to ten days for complete cure. In addition, solvent solutions used for dip application, because of the moisture curing, quickly turn cloudy due to precipitated polymer resulting from reaction of the MDX-4-4159 with humidity in the air. Dipping solutions must be replaced frequently which is time consuming, wasteful and costly.

In U.S. Pat. No. 4,904,433, Williamitis discloses a method for catheter tipping which includes applying a noncuring aminoalkyl terminated polysiloxane to a catheter blank, mounting the coated blank over a mandrel, advancing the mandrel into a heated die for tipping and removing the tipped catheter from the die and the mandrel.

There is a need for a polysiloxane composition capable of lubricating metal surfaces which overcomes migration and wipe away problems by adsorbing firmly and quickly without a need for cure time. The present invention addresses this need.

SUMMARY OF THE INVENTION

Articles having a metal surface intended to come into moving contact with another surface have a coating of a noncuring polysiloxane lubricant substituted with a polar group, hereinafter referred to as the polar lubricant. The article may have an edge for cutting, such as a blade, a point for puncturing, such as a , needle or cannula, or it may be intended for sliding contact with the other surface, such as a cannula or guidewire. Preferred polar lubricants are noncuring polysiloxanes terminated with an amino or carboxy group. The most preferred polar lubricant is an aminopropyl terminated polysiloxane of viscosity about 2,000.

In another aspect of the invention, a catheter assembly includes the lubricated cannula or guidewire and a mated plastic catheter tubing. The tubing may also be coated with the polar lubricant or preferably with a nonpolar polysiloxane lubricant. The preferred lubricant for the catheter portion of the assembly is a trialkylsiloxy terminated polysiloxane of the DC ®360 series.

The metal article coated with the noncuring polar lubricant has improved lubricity compared to an article coated with a conventional lubricant. Because of the polar group, the lubricant is adsorbed into the metal and adheres to the surface so that wipe away is significantly reduced. Thus, when the hypodermic needle of the invention is inserted through the skin, the lubricant remains adherent and is thus available as a lubricant when the needle is retracted. In contrast, a metal needle lubricated with a conventional lubricant suffers significant wipe away so that very little is left for retraction. Additional pain is experienced by the patient due to the friction between the substantially bare needle and the skin. Similarly, other cutting devices, such as surgical blades, cannulas and lancets may be used with less pain for the patient due to the enhanced retention of the noncuring polar lubricant.

It is evident that articles intended for multiple use, such as razor blades, may also benefit from the noncuring polar lubricant. Currently used lubricants for blades are of polytetrafluoroethylene or fluorinated waxes which require high temperature curing or silicones such as MDX-4-4159 which require moisture curing. The polar lubricant of the blade of the invention is noncuring, of low viscosity so that it remains a liquid, and is easily applied in a thin economical coating. Because of its adhering property, more shaves of greater comfort can be performed before the lubricant is removed and the blade loses its edge.

For metal articles used in sliding contact with a plastic surface, such as catheter guidewires, the noncuring polar lubricant reduces the drag force which routinely develops, particularly in turns or bends. Thus, after catheter placement, the guidewire may easily be removed without application of excess force to overcome the drag, which, with conventional lubricants, often leads to "stick slip," loss of catheter placement and danger to the patient.

BRIEF DESCRIPTION OF THE DRAWING

The FIGURE illustrates a lubricated catheter assembly of the invention including a cannula and catheter tubing.

DETAILED DESCRIPTION

While this invention is satisfied by embodiments, in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

In accordance with the present invention, articles are lubricated with the polar lubricant, i.e., a noncuring polysiloxane lubricant having a polar terminal group. Preferred articles are metal articles. While the invention contemplates lubrication of articles of any metal, preferably steel, the most preferred articles are of stainless steel. It is believed, although not yet substantiated, that the polar lubricant, while noncuring, is adherent to the article because the polar group causes adsorption into the article surface.

Representative nonlimiting metal articles contemplated to be lubricated with the polar lubricant of the invention are blades such as scalpels, razor blades and surgical blades, hypodermic needles, such as syringe needles, lancets and any metal catheter insertion device. The term catheter insertion device is intended to include devices for skin puncture and catheter placement. The skin puncture device may be a cannula or a catheter needle portion which is unitary with a plastic catheter tubing. The term cannula will hereinafter be used generically to define any metal device for skin puncture used with a catheter tubing. The term catheter placement device includes any metal device, such as a guidewire or a stylet used to advance or position a catheter tubing after insertion, The term guidewire will hereinafter be used generically to define catheter placement devices.

Thus, in one preferred embodiment of the invention, the metal article includes a cutting edge, such as a surgical blade, having the polar lubricant coated thereon. Another preferred embodiment is a metal article having a cutting point for puncture of a membrane, preferably skin, such as a cannula or needle, having the polar lubricant coated thereon.

It is not intended that the metal article be limited to cutting or puncturing devices. Thus, still another preferred embodiment of the invention is a catheter guidewire coated with the polar lubricant.

The guidewire or the cannula may be part of a catheter assembly which includes a catheter portion. For this embodiment of the invention, a coated cannula may be used to puncture the skin of a patient and the catheter portion then inserted at the puncture site. After removal of the cannula, the coated quidewire may be passed down the catheter and used to advance or position the catheter to the desired location in a patient's vein or artery.

The catheter portion of the assembly may preferably be plastic. Any polymer as known in the art may be used for the catheter portion of the assembly. Without being limited thereby, the catheter may be of polyolefin, polyvinyl, polyester, polyamide and preferably polyurethane.

In accordance with the invention, it has been found that any of the cannula, guidewire and catheter portions of the assembly may have a coating of the polar lubricant. However, it has been found that a noncuring nonpolar polysiloxane is a more effective lubricant on plastic articles. Thus, the most preferred assembly of the invention includes the cannula or guidewire having a coating of the polar lubricant positioned inside a plastic catheter tubing having a coating of the nonpolar lubricant on the outside surface thereof.

The Figure illustrates one embodiment of an assembly 10 of the invention. A steel cannula 12 has body portion 14 and tip 16. Tip 16 and preferably at least part of body portion 14 has a coating 18 of the polar lubricant thereon. The coated cannula fits inside of a plastic catheter tubing 20. In general, the catheter is two gauge sizes larger than the cannula. Catheter tubing 20 preferably has a taper 22 at its forward end for additional patient comfort during insertion through the puncture site formed by tip 16. A coating 24 of noncuring nonpolar lubricant on tubing 20 provides patient comfort during insertion and withdrawal of the catheter through the puncture site.

The polar lubricants contemplated by the present invention are noncuring polysiloxanes substituted with a polar group. The polar group may be pendant or terminal. In preferred polar lubricants, the polar group is terminal and may be represented by the formula

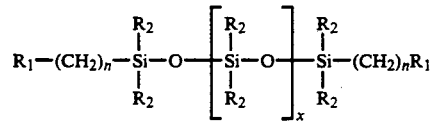

wherein $R_1$ may be OH, $NH_2$,

or COOH, $R_2$ may be lower alkyl of 1 to 4 carbon atoms, n may be 2 to 4, and x is an integer sufficient to give the lubricant a viscosity of about 10 to 2,000,000 ctsk. In preferred lubricants, $R_1$ is $NH_2$ or COOH, $R_2$ is $CH_3$ and the viscosity is 100 to 100,000 ctsk. The most preferred lubricants are aminopropyl terminated polydimethyl siloxanes of viscosity 300 to 25,000 ctsk. These products, known in the art s intermediate for polymer synthesis, are commercially available from Petrarch Systems, Bristol, Pa. The invention will henceforth be described in terms of the commercial aminopropyl terminated Petrarch product PS513 of viscosity 2,000 ctsk.

The noncuring nonpolar lubricant for the catheter portion of the assembly may be a conventional trimethylsiloxy terminated polysiloxane. These products are well-known and a wide variety of products ranging in viscosity from 0.65 to 2,500,000 are commercially available from Petrarch Systems. Particularly preferred nonpolar lubricants are the DC®360 medical grade polydimethylsiloxanes ranging in viscosity from 20 to 12,500 commercially available from Dow Corning Corp., Midland, Mich. The most preferred nonpolar lubricant is DC®360 fluid of viscosity 12,500.

The lubricants may be applied to the article by any conventional procedure such as wiping, spraying, roll coating, printing or preferably by dipping. The article may be dipped into neat lubricant or preferably into a 0.1 to 10, most preferably into a 0.5 to 3 weight percent solution of the lubricant in an appropriate solvent. Suitable solvents are alcohols, alkanes, chlorocarbons and preferably chlorofluoro carbons. The most preferred solvent is FREON TF®.

The thickness of the coating may vary from about 10 to 50 µ depending on factors such as the concentration of lubricant in the solvent, the temperature of the solvent solution, and the rate of withdrawal from the solution. The rate of withdrawal may be about 5 to 30, preferably 10 to 15 ft/min.

The effectiveness of the polar lubricants on metal articles may be tested for penetration, drag, retract and adhesion forces using a Model 1122 Instron Universal Testing Machine and a natural rubber test membrane The drag force is the frictional force between a needle and the membrane after the needle has punctured the membrane and is continued to be moved forward. The retract force is the force required to slide the needle backward through the membrane when withdrawing the needle. Adhesion is defined as the tendency of two surfaces in stationary contact to develop a degree of adherence to each other.

The following examples are provided to further describe the invention but are not to be considered as limitative of the invention.

EXAMPLE I

Lubricating solutions (2.5 wt %) in FREON TF® were prepared with the following lubricants:
1. AP-50[a]
2. AP-2000[b]
3. 75% AP-50; 25% AP-2000
4. 50% AP-50; 50% AP-2000
5. 25% AP-50; 75% AP-2000
6. CP[c]
7. 50% AP-2000; 50% CP
8. DC®360 a—aminopropyl terminated polydimethylsiloxane viscosity 50 ctsk.
b—aminopropyl terminated polydimethylsiloxane, viscosity 2,000 ctsk.
c—carboxypropyl terminated polydimethylsiloxane, viscosity 2,000 ctsk.

Five 18 gauge stainless steel needles were dipped into each lubricating solution, withdrawn, and the solvent flashed off. The needles were then mounted vertically on the Instron and the force required for initial needle penetration, needle drag after penetration, and needle retraction were measured through 1/16 inch natural rubber sheet held on the Instron at 45° to the needle.

The following data, averaged for the five needles, given in grams, was obtained:

TABLE I

| Lubricating Solution | Needle Tip Penetration | Needle Drag | Needle Retraction |
|---|---|---|---|
| Solvent only | 286.5 ± 25.2 | 247.2 ± 21.8 | 195.8 ± 20.2 |
| 1 | 182.2 ± 19.6 | 57.3 ± 4.8 | 62.0 ± 5.7 |
| 2 | 155.2 ± 18.7 | 50.0 ± 1.8 | 50.4 ± 1.9 |
| 3 | 178.5 ± 9.9 | 39.8 ± 8.2 | 45.3 ± 4.7 |
| 4 | 187.2 ± 12.0 | 42.3 ± 3.3 | 46.9 ± 6.7 |
| 5 | 177.7 ± 4.5 | 34.5 ± 2.5 | 45.3 ± 4.8 |
| 6 | 181.8 ± 7.2 | 32.8 ± 1.8 | 43.7 ± 4.0 |
| 7 | 167.9 ± 6.2 | 26.7 ± 3.0 | 38.6 ± 2.7 |
| 8 | 182.3 ± 16.0 | 25.0 ± 1.0 | 55.0 ± 2.0 |

The above data shows lower penetration forces for the needles lubricated with the polar lubricant compared to forces measured without lubricant or with nonpolar lubricant.

EXAMPLE II

Stainless steel cannulas (18, 22 and 24 gauge) were dipped into a FREON TF® solution of lubricant, the FREON TF® flashed off and the lubricated cannulas inserted into 16, 20 and 22 gauge INSYTE® polyurethane catheters. Fifteen cannula catheter assemblies of each gauge size and each lubricant were prepared. The assemblies were then dipped into a FREON TF® solution of lubricant to coat the catheters and the FREON-TF® flashed off.

P 2106

The assemblies with the needle tips protruding beyond the end of the catheter were mounted on the Instron Model 1122 Universal Testing Machine and the force required to cause penetration of the needle, penetration of the catheter, catheter drag and catheter retract through 1/16 inch rubber sheet were measured with the Instron. The average data for the 15 assemblies is tabulated below and compared with forces measured with unlubricated assemblies.

TABLE II

| LUBRICANT - %[a] | | Cannula Penetration gr. | | | Catheter Penetration gr. | | | Catheter Drag gr. | | | Catheter Retraction gr. | | |
|---|---|---|---|---|---|---|---|---|---|---|---|---|---|
| | | | | | Gauge Size | | | | | | | | |
| On Cannula | On Catheter | 18 | 22 | 24 | 16 | 20 | 22 | 16 | 20 | 22 | 16 | 20 | 22 |
| none | none | 217 | 177 | 139 | 141 | 107 | 89 | 95 | 78 | 73 | 178 | 145 | 153 |
| PDMS[b] - 2.4 | PDMS[c] - 2.0 | | 124 | 110 | | 62 | 57 | | 27 | 21 | | 45 | 33 |
| AP-2000 - 2.5 | AP-2000 - 2.5 | 168 | 107 | 102 | 102 | 65 | 61 | 56 | 37 | 27 | 82 | 49 | 40 |
| AP-2000 - 1.5 | AP-2000 - 1.5 | 172 | 107 | 100 | 122 | 75 | 70 | 84 | 55 | 42 | 99 | 59 | 46 |
| AP-2000 - 1.0 | AP-2000 - 1.0 | 174 | 109 | 107 | 126 | 92 | 80 | 85 | 59 | 49 | 100 | 62 | 54 |
| AP-2000 - 0.5 | AP-2000 - 0.5 | 167 | 114 | 109 | 125 | 95 | 84 | 76 | 61 | 51 | 94 | 62 | 56 |
| AP-2000 - 0.5 | PDMS[c] - 2.0 | | 89 | 98 | | 50 | 58 | | 22 | 21 | | 34 | 32 |
| CP - 0.5 | PDMS[c] - 2.0 | | 112 | 96 | | 67 | 56 | | 25 | 20 | | 49 | 32 |
| CP - 2.0 | CP - 2.0 | | 116 | 92 | | 71 | 62 | | 29 | 29 | | 50 | 41 |
| CP - 0.5 | CP - 2.0 | | | 89 | | | 58 | | | 24 | | | 36 |
| CP - 0.5 | CP - 0.5 | | | 110 | | | 63 | | | 25 | | | 38 |

[a]percentage of lubricant in FREON-TF® dipping solution
[b]viscosity 1,000,000
[c]viscosity 12,500

The above data shows clearly that the force required for needle penetration is lower on lubrication with the polar lubricant than with the nonpolar lubricant. On the other hand, the force required for catheter penetration, drag and retraction, while reduced over the control with polar lubricant, is seen to be even lower when the assembly is lubricated with the nonpolar lubricant.

EXAMPLE III

Blade Lubrication—Single Cut

A piece of 16 gauge polyurethane catheter tubing was clamped firmly onto a hollow, circular anvil. Ten commercial single edge razor blades (3 Hyde, 7 Gem super stainless) were held in the jaw of the Instron and lowered until contact with the tubing was established. The force required to cut the tubing at an angle of 90° was measured by the Instron.

The blades were tested, A, as received; B, as received and cleaned by a two hour reflux in FREON TF ® and drying; C, after dip coat lubrication with 2.4 weight percent of PDMS of 1,000,000 viscosity; and D, after dip coat lubrication with 2.5 weight percent of AP-2000. The individual penetration forces were averaged to give the following results:

TABLE III

| Blade | Penetration Force, grs. | | | |
|---|---|---|---|---|
| | A | B | C | D |
| Hyde | 680 | 680 | 676 | 440 |
| Gem | 379 | 366 | 344 | 294 |

The above data shows only marginal reduction in force using blades lubricated with PDMS 1,000,000 because the lubricant pools on the surface of the tubing. In contrast, blades lubricated with the adherent polar lubricant show substantially reduced forces required for cutting.

EXAMPLE IV

Blade Lubrication—Multiple Cuts

Using the equipment of Example III, the penetration force for a Gem super stainless blade coated with 2.5 weight percent AP-2000 was measured after 33 consecutive cuttings. The following results were obtained:

TABLE IV

| Cut Number | Penetration Force, gm |
|---|---|
| 1 | 209 |
| 2 | 217 |
| 3 | 319 |
| 4 | 389 |
| 10 | 402 |
| 20 | 433 |
| 30 | 453 |
| 33 | 453 |

EXAMPLE V

Plain Guidewire Lubrication

Stainless steel guidewires (noncoiled) were triple rinsed in FREON-TF ® and allowed to dry. Twelve wires were dipped into a 2.0 weight percent solution PDMS of viscosity 12,500 in FREON-TF ® and the solvent flashed off. Another 12 wires were dip coated in the same way from a 2.0 weight percent solution of AP-2000.

The wires were then inserted into 24 gauge polyurethane catheters and set aside at ambient temperature. After 24 hours, the pullout force required to overcome friction was measured on the Instron using the "J" fixture apparatus to drag the wire around a 1 inch radius 180° bend. The average pullout force for the PDMS coated wires was 35 g. The average pullout force for the AP-2000 coated wires was 12.7 g.

This data clearly shows that drag of the wire against the plastic catheter is substantially less when lubrication is performed with the polar lubricant compared to the nonpolar lubricant.

EXAMPLE VI

Coiled—Guidewire Lubrication

In the same way as described in Example V, six each coiled stainless steel guidewires were lubricated with 2% FREON TF ® solutions of DC ®360 (nonpolar lubricant) and with 2.0, 1.0 and 0.5% AP-2000 (polar lubricant), with and without precleaning with FREON TF ®. Using the Instron, the force required to extract the coiled guidewire from the catheter was measured. The following data was obtained:

TABLE VI

| RINSING | LUBRICANT - % | FORCE, gr |
|---|---|---|
| − | None | 69 ± 18 |
| + | None | 162 ± 36 |
| − | PDMS - 2.0 | 22 ± 4 |
| + | PDMS - 2.0 | 35 ± 5 |
| − | AP-2000-2.0 | 14 ± 4 |
| + | AP-2000-2.0 | 19 ± 1 |
| − | AP-2000-1.0 | 15 ± 1 |
| − | AP-2000-0.5 | 17 ± 2 |
| + | AP-2000-0.5 | 21 ± 2 |

It is seen from the data that guidewire extraction requires less force after lubrication with polar lubricant.

EXAMPLE VII

Adhesion Study—Cannula Catheter

Seven stainless steel cannulas each of six gauge were lubricated with 0.5% FREON TM solutions of AP-2000 and PDMS of 12,500 viscosity. The lubricated cannulas were assembled into tipped polyurethane catheters of 2 gauge sizes larger and acceleration aged at 250° C. to simulate a five year shelf life. Using the Instron, the force required to separate the cannula and cathete tips was measured. The following data was obtained:

TABLE VII

| CANNULA GAUGE SIZE | SEPARATION FORCE | |
|---|---|---|
| | AP-2000 | PDMS |
| 14 | 271 ± 51 | 544 ± 89 |
| 16 | 201 ± 32 | 211 ± 97 |
| 18 | 423 ± 78 | 413 ± 67 |
| 20 | 155 ± 75 | 364 ± 52 |
| 22 | 83 ± 38 | 255 ± 59 |
| 24 | 107 ± 60 | 251 ± 92 |

It is seen from the data that cannula separation requires less force after lubrication with polar lubricant.

What is claimed is:

1. An article comprising a metal surface having thereon a coating of a noncuring polysiloxane lubricant substituted with an aminoalkyl group, said polysiloxane lubricant having a viscosity of about 300 to 25,000 centistokes.
2. The article of claim 1 which is a guidewire.
3. The article of claim 1 which is a cannula.
4. The article of claim 1 which is a blade.
5. The article of claim 1 wherein said polysiloxane lubricant is terminated with said aminoalkyl group.

6. An article comprising a metal surface having thereon a coating of a noncuring polysiloxane lubricant substituted with an amino group, said polysiloxane lubricant having a viscosity of about 100 to 60,000 centistokes.

7. An article comprising a metal surface having thereon a coating of a noncuring aminopropyl terminated polysiloxane lubricant having a viscosity of about 1,000 to 2,000.

8. An assembly comprising a plastic catheter, a coating of a lubricant on said catheter, a metal article within said catheter and a coating of a noncuring aminoalkyl terminated polysiloxane lubricant on said article, said polysiloxane lubricant having a viscosity of about 300 to 25,000 centistokes.

9. The assembly of claim 8 wherein said catheter is of a polymer selected from the group consisting of polyolefin, polyvinyl, polyester, polyamide and polyurethane.

10. The assembly of claim 9 wherein said article is a guidewire.

11. The assembly of claim 9 wherein said article is a cannula.

12. An assembly comprising a plastic catheter, a coating of a lubricant on said catheter, a metal article within said catheter and a coating of a polysiloxane lubricant substituted with an amino group on said article, said polysiloxane lubricant having a viscosity of about 100 to 60,000 centistokes.

13. An assembly comprising a metal article, a coating of a polysiloxane lubricant terminated with an aminopropyl group on said article, a plastic catheter positioned over said article and a coating of a noncuring, polysiloxane lubricant terminated with a trialkylsiloxy group on said catheter, said lubricant on said article having a viscosity of about 1,000 to 2,000.

14. The assembly of claim 13 wherein said article is a guidewire.

15. The assembly of claim 13 wherein said article is a cannula.

* * * * *